United States Patent
Subbarao et al.

(10) Patent No.: US 7,652,265 B2
(45) Date of Patent: Jan. 26, 2010

(54) AIR TREATMENT SYSTEM

(75) Inventors: Gautam Subbarao, Louisville, KY (US); Mark Wayne Wilson, Simpsonville, KY (US); Anand Ganesh Joshi, Hyderabad (IN); Hemachandran Umakanthan, Cuddalore (IN); Ramnath Vaidyanathan, Andhra Pradesh (IN)

(73) Assignee: General Electric Company, Schenectady, NY (US)

( * ) Notice: Subject to any disclaimer, the term of this patent is extended or adjusted under 35 U.S.C. 154(b) by 127 days.

(21) Appl. No.: 11/636,757

(22) Filed: Dec. 11, 2006

(65) Prior Publication Data

US 2008/0134899 A1  Jun. 12, 2008

(51) Int. Cl.
*H01J 37/20* (2006.01)

(52) U.S. Cl. .............. 250/437; 250/432 R; 250/455.11; 250/504 R; 250/428; 96/223; 96/224; 424/121

(58) Field of Classification Search ................. 250/528, 250/431, 432 R, 435, 436, 437, 455.11, 504 R; 96/223, 224; 424/121
See application file for complete search history.

(56) References Cited

U.S. PATENT DOCUMENTS

| | | | | |
|---|---|---|---|---|
| 3,757,495 A * | 9/1973 | Sievers | .......................... | 96/121 |
| 4,806,768 A | 2/1989 | Keutenedjian | | |
| 5,112,370 A * | 5/1992 | Gazzano | ...................... | 422/121 |
| 5,330,722 A * | 7/1994 | Pick et al. | ....................... | 96/55 |
| 5,523,057 A * | 6/1996 | Mazzilli | ...................... | 422/121 |
| 5,601,786 A * | 2/1997 | Monagan | ..................... | 422/108 |
| 5,612,001 A * | 3/1997 | Matschke | ...................... | 96/224 |
| 5,656,242 A * | 8/1997 | Morrow et al. | ................. | 96/224 |
| 5,759,239 A | 6/1998 | Yu | | |
| 5,837,207 A | 11/1998 | Summers | | |
| 5,997,619 A * | 12/1999 | Knuth et al. | ................... | 96/224 |
| 6,221,314 B1 * | 4/2001 | Bigelow | ........................ | 422/24 |
| 6,500,387 B1 * | 12/2002 | Bigelow | ........................ | 422/24 |
| 6,805,733 B2 * | 10/2004 | Engel et al. | .................... | 96/224 |
| 6,818,177 B1 | 11/2004 | Turcotte | | |
| 6,855,295 B2 * | 2/2005 | Kulp | ........................... | 422/121 |
| 6,875,988 B1 * | 4/2005 | Sauska et al. | .......... | 250/455.11 |
| 7,005,111 B2 * | 2/2006 | Bollini | ........................ | 422/121 |
| 7,175,814 B2 * | 2/2007 | Dionisio | ...................... | 422/121 |
| 7,303,612 B2 * | 12/2007 | Morrow et al. | ................. | 96/224 |
| 2002/0088945 A1 * | 7/2002 | Matschke | ............... | 250/432 R |
| 2003/0049809 A1 * | 3/2003 | Kaiser et al. | ............. | 435/173.1 |
| 2008/0019861 A1 * | 1/2008 | Silderhuis | ....................... | 422/3 |

* cited by examiner

*Primary Examiner*—David A Vanore
*Assistant Examiner*—Michael Maskell
(74) *Attorney, Agent, or Firm*—George L. Rideout, Esq.; Armstrong Teasdale LLP

(57) ABSTRACT

An air treatment system includes a housing defining a chamber, and an ultraviolet lamp positioned within the chamber. The housing further defines an air inlet at a first end portion of the housing and an air outlet at a second end portion of the housing opposing the first end portion. The chamber provides flow communication between the air inlet and the air outlet. At least one ultraviolet lamp is positioned within the chamber. The at least one ultraviolet lamp is positioned about a first axis and includes a first end and a second end spaced with respect to the first end along the first axis. The at least one ultraviolet lamp is configured for facilitating inactivating contaminants within air channeled through the chamber.

19 Claims, 3 Drawing Sheets

AIR TREATMENT SYSTEM

BACKGROUND OF THE INVENTION

This invention relates generally to air purification and treatment and, more particularly, to systems and methods for purifying and treating air.

At least some conventional air purification apparatus include a housing defining a chamber. An inlet air duct is positioned at a first end of the chamber and an outlet air duct is positioned at an opposing second end of the chamber. A plurality of ultraviolet lamps are positioned within the chamber. Each lamp is coupled to a lamp holder mounted within the chamber to hold the lamp stationary within the chamber. A corresponding ballast and harness electrically couples the lamp to an electrical source for energizing the lamp. During operation, unpurified air is channeled through the chamber. The ultraviolet lamps are energized to generate ultraviolet light, which purifies the air as the air moves through the chamber. In at least some conventional air purification apparatus, ultraviolet light is able to travel through the air ducts to undesirably escape from the chamber. The escaped ultraviolet light may promote the degradation of plastic duct material and may also produce an undesirable glow along the duct work.

Additionally, the plurality of ultraviolet lamps and the corresponding electrical components occupy a considerable amount of space within the chamber and require a sufficiently large air purification apparatus chamber. Moreover, the arrangement of the ultraviolet lamps and corresponding electrical components prevents or limits a uniform ultraviolet density within the chamber. To compensate for the nonuniform ultraviolet density within the chamber, an ultraviolet light reflective layer is coated on an inner surface of the chamber to improve the ultraviolet density uniformity, which undesirably increases manufacturing time and/or cost.

BRIEF DESCRIPTION OF THE INVENTION

In one aspect, an air treatment system is provided. The air treatment system includes a housing defining a chamber. The housing further defines an air inlet at a first end portion of the housing and an air outlet at a second end portion of the housing opposing said first end portion. The chamber provides flow communication between the air inlet and the air outlet. At least one ultraviolet lamp is positioned within the chamber. The at least one ultraviolet lamp is positioned about a first axis and includes a first end and a second end spaced with respect to the first end along the first axis. The at least one ultraviolet lamp is configured for facilitating inactivating contaminants within air channeled through the chamber.

In another aspect, an air treatment system is provided. The air treatment system includes a housing defining a chamber. The housing further defines an air inlet at a first end portion of the housing and an air outlet at a second end portion of the housing opposing the first end portion. The chamber provides flow communication between the air inlet and the air outlet. At least one ultraviolet lamp is positioned within the chamber. The at least one ultraviolet lamp is configured for facilitating inactivating contaminants within air channeled through the chamber. A light trap is coupled to the housing with respect to at least one of the air inlet and the air outlet. The light trap is configured to prevent light generated by the at least one ultraviolet lamp from exiting said housing.

In another aspect, an air treatment system is provided. The air treatment system includes a housing defining a chamber along a first axis. The housing further defines an air inlet and an air outlet. The chamber provides flow communication between the air inlet and the air outlet. At least one ultraviolet lamp including a helical tube is positioned within the chamber and extends about the first axis in a first translational direction. The at least one ultraviolet lamp is configured for facilitating inactivating contaminants within air channeled through the chamber.

In still another aspect, a method for assembling an air treatment system is provided. The method includes providing a housing defining a chamber along a first axis. The housing further includes an air inlet at a first end portion of the chamber and an air outlet at a second end portion of the chamber. The chamber defines an air passage providing flow communication between the air inlet and the air outlet. At least one ultraviolet lamp is positioned within the air passage. The at least one ultraviolet lamp is positioned about the first axis and includes a first end and a second end spaced with respect to the first end along the first axis. The at least one ultraviolet lamp is configured for facilitating inactivating contaminants within air channeled through the air passage.

DETAILED DESCRIPTION OF THE INVENTION

Figure 1:
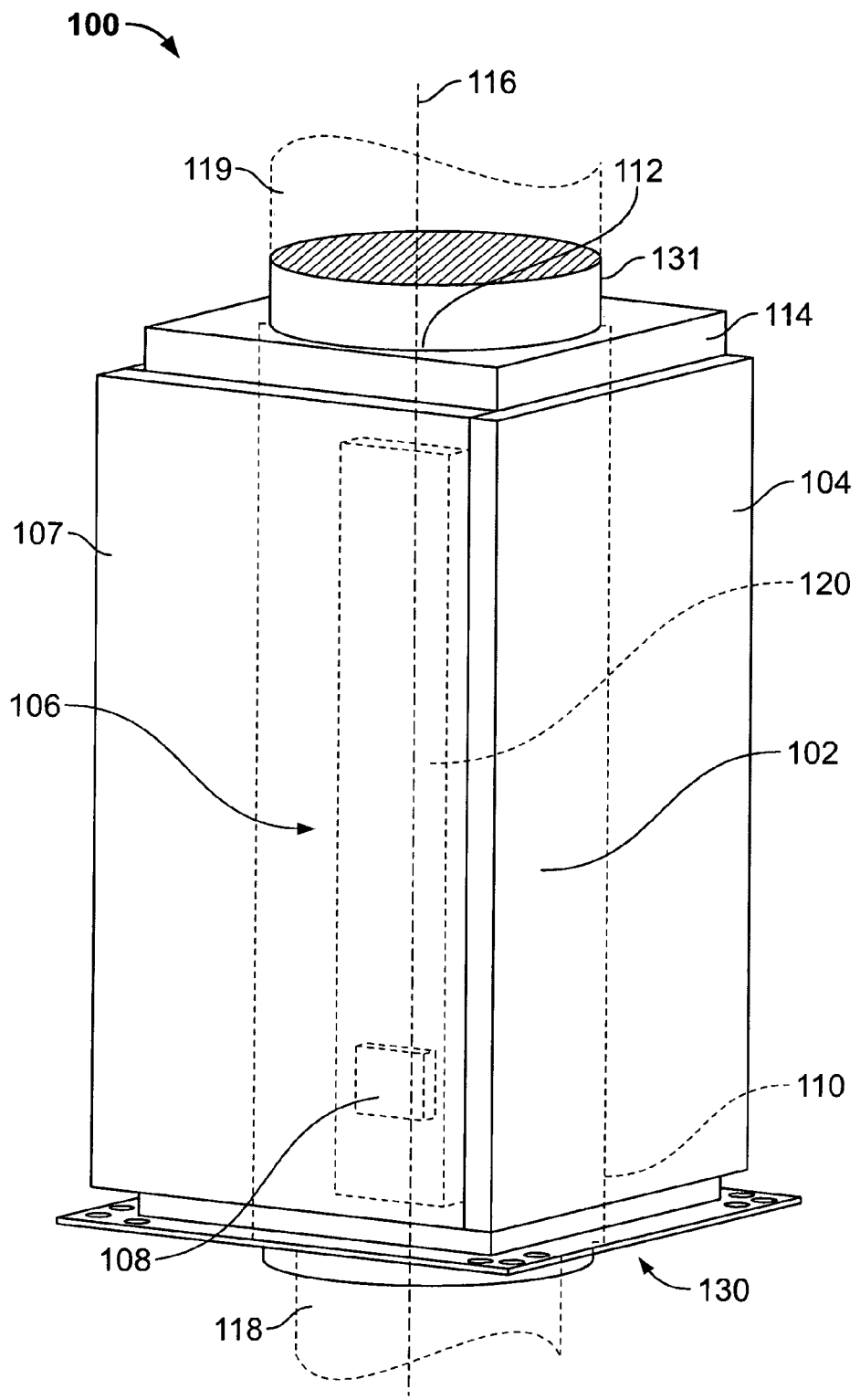
FIG. 1 is a perspective view of an exemplary air treatment apparatus.

FIG. 1 is a perspective view of an exemplary air treatment apparatus 100. Air treatment apparatus 100 is suitable for use with any suitable air treatment system including, without limitation, an air conditioning system (not shown), for inactivating and/or removing contaminants such as bacteria and/or microbes within air channeled through air treatment system 100. In one embodiment, air treatment apparatus 100 includes a housing 102 having a generally cylindrical shape that forms a sidewall 104 defining a chamber 106. In alternative embodiment, housing 102 may have any suitable shape forming any suitable number of sidewalls. Housing 102 also defines an air inlet 108 at a first end 110 of chamber 106 and an air outlet 112 at a second end 114 of chamber 106 opposing first end portion 110. Chamber 106 extends along a longitudinal central axis 116 of housing 102 between air inlet 108 and air outlet 112 to provide air flow communication therebetween. Air inlet 108 is coupled in flow communication to a first duct portion 118 and air outlet 112 is coupled in flow communication with duct 119 of a suitable air conditioning system, for example.

In the exemplary embodiment, at least one ultraviolet lamp 120 is positioned within chamber 106. Ultraviolet lamp 120 is electrically coupled to an electrical source, as described in greater detail below. The electrical source energizes ultraviolet lamp 120 to generate ultraviolet light within chamber 106. A first light trap 130 is mounted to housing 106 at first end 110 to cover air inlet 108 and a second light trap 131 is mounted to housing 106 at second end 114 to cover air outlet 112 for facilitating preventing or limiting the ultraviolet light from exiting air inlet 108 and/or air outlet 112. It is apparent to those skilled in the art and guided by the teachings herein provided that light traps 130 and/or 131 can be mounted within or outside of the respective air inlet 108 and air outlet 112 for facilitating preventing or limiting the ultraviolet light from exiting air inlet 108 and/or air outlet 112.

Figure 2:
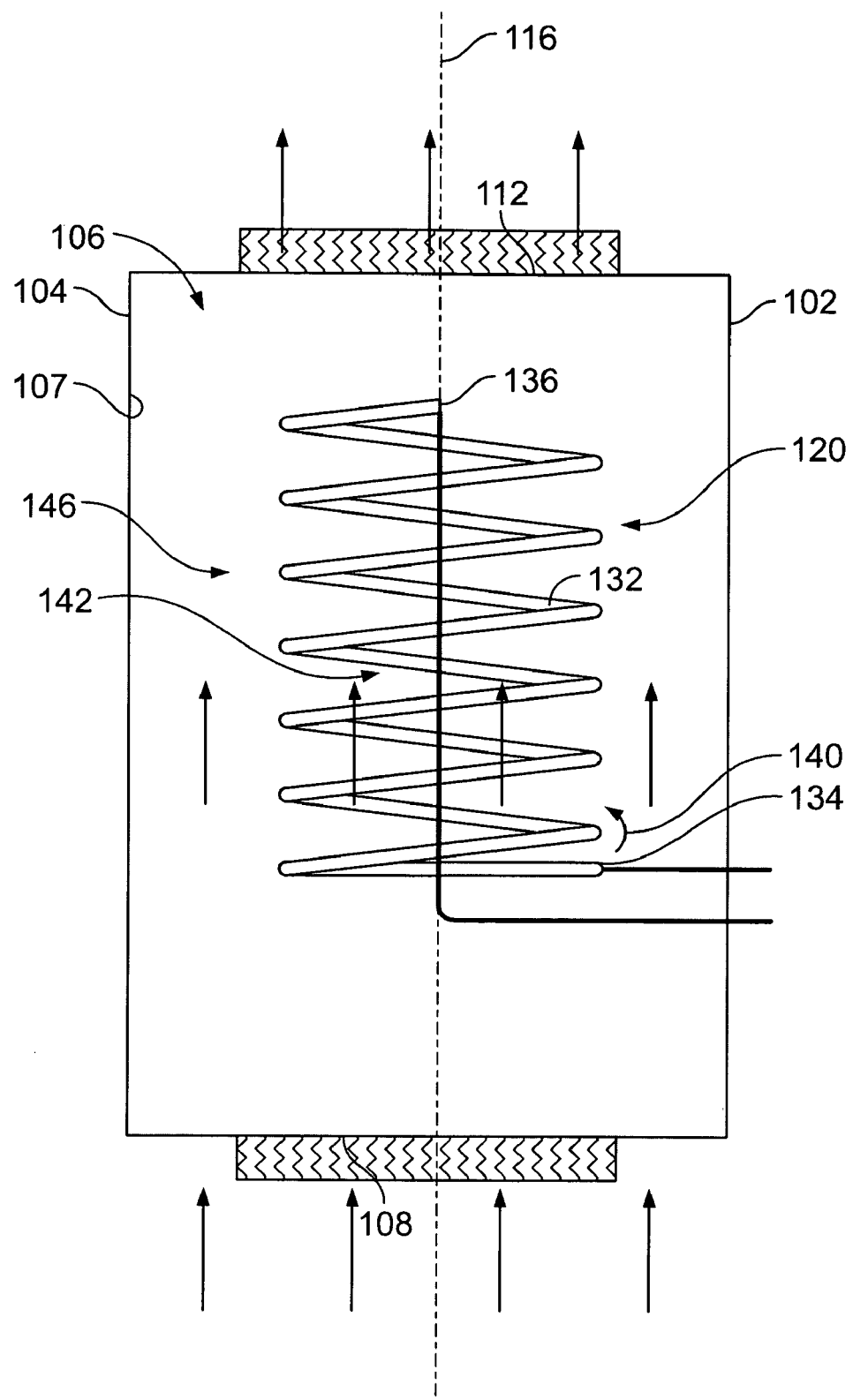
FIG. 2 is a schematic sectional view of an air treatment apparatus including an exemplary ultraviolet lamp mounted within a chamber defined by the air treatment apparatus.

FIG. 2 is a schematic plan view of exemplary ultraviolet lamp 120 mounted within chamber 106. As shown in FIG. 2, ultraviolet lamp 120 is substantially helical in shape, and includes a tubular body 132 having a first end 134 and a second end 136 spaced with respect to first end 134 along central axis 116 of housing 102. In one embodiment, ultraviolet lamp 120 is electrically coupled to a power source (no shown) at first end 134 and second end 136. As such, ultraviolet lamp 120 is energized to generate ultraviolet light within chamber 106 for facilitating inactivating and/or removing contaminants from the air channeled through chamber 106.

In the exemplary embodiment, body 132 extends about central axis 116 in a translational direction 140 to define an inner passage 142 within ultraviolet lamp 120. Further, as shown in FIG. 2, body 132 is spaced with respect to inner surfaces 107 of sidewall 104 to define an outer passage 146 between ultraviolet lamp 120 and side wall 104 in addition to or in lieu of inner passage 142. The helical shape of ultraviolet lamp 120 increases the ultraviolet intensity per unit length of ultraviolet lamp 120 when compared to conventional straight or non-helically shaped ultraviolet lamps such that air can flow through inner passage 142 and/or outer passage 146.

In the exemplary embodiment, outer passage 146 surrounds ultraviolet lamp 120 and cooperates with inner passage 142 to facilitate channeling air through chamber 106 between air inlet 108 and air outlet 112. In alternative embodiments, ultraviolet lamp 120 is not necessarily positioned about central axis 116 and/or does not necessarily have a helical shape. Further, at least one ultraviolet lamp 120 may be positioned within chamber 106 as desired to define inner passage 142 and/or outer passage 146. In a further alternative embodiment, a plurality of ultraviolet lamps 120 are positioned within chamber 106.

Figure 3:
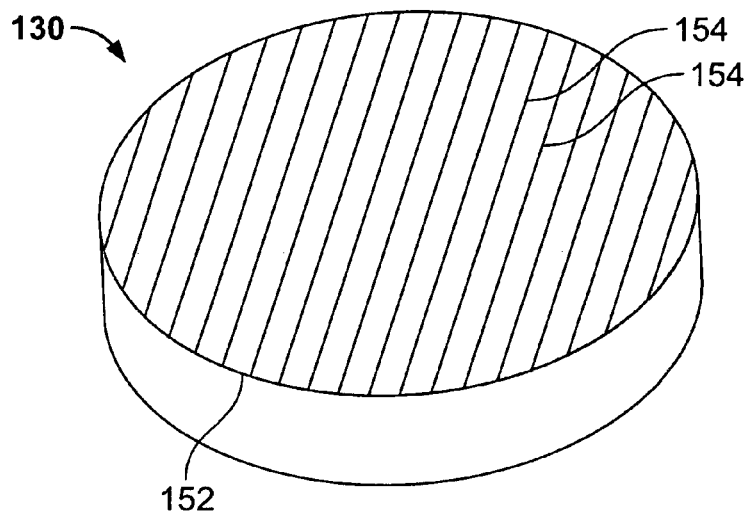
FIG. 3 is a perspective view of an exemplary light trap suitable for use with the air treatment apparatus shown in FIG. 1.
Figure 4:
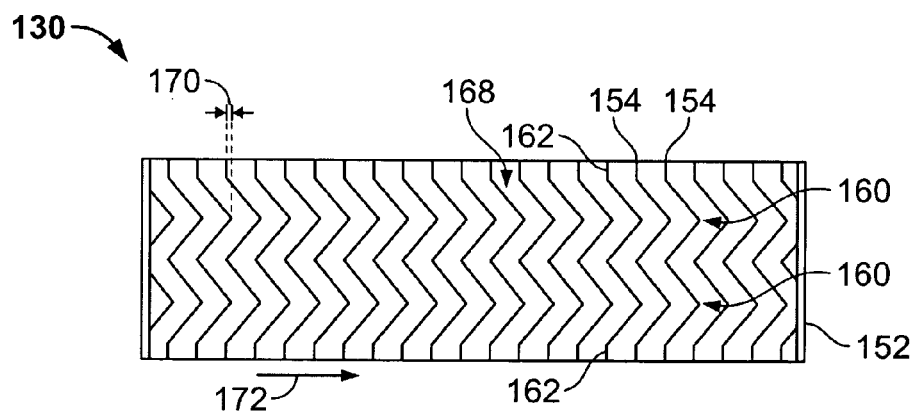
FIG. 4 is a sectional view of the light trap shown in FIG. 3.

FIG. 3 is a perspective view of light trap 130 suitable for use with air treatment apparatus 100 shown in FIG. 1. FIG. 4 is a sectional view of light trap 130 shown in FIG. 3.

In the exemplary embodiment, light trap 130 (and/or light trap 131) is made of a suitable material that withstands degradation due to exposure to ultraviolet light. Light trap 130 includes a disc-shaped body 152 surrounding a plurality of integrated elongated baffle elements 154. In one embodiment, body 152 and/or baffle elements 154 are fabricated of a light absorbing material or a light reflective material, such as aluminum, for facilitating preventing the ultraviolet light from escaping chamber 106. In an alternative embodiment, body 152 and/or baffle elements 154 are coated with a light absorbing material, such as an ultraviolet light absorbing material or a black paint, or a light reflective material. The light absorbing material or coating absorbs at least a portion of the ultraviolet light while the light reflective material or coating reflects at least a portion of the ultraviolet light back into chamber 106 and/or against another surface of body 152 and/or baffle elements 154 to reduce the intensity of the ultraviolet light.

As shown in FIG. 4, baffle elements 154 are substantially identical in cross section. Adjacent baffle elements 154 are configured to define a tortuous path through which air is able to travel but through which light is prevented from traveling. In one embodiment, each baffle element includes a plurality of angled wall portions 160, as shown in FIG. 4, and end wall portions 162 generally parallel with an inner surface of body 152. End wall portion 162 transition into a respective angled wall portion 160. Angled wall portions 160 transitions into adjacent angled wall portions 160 such that adjacent wall portions are positioned at an angle with respect to each adjacent angled wall portion 162. In one embodiment, each angled wall portion transitions into an adjacent angled wall portion at an angle of about 30° to about 150°. In an alternative embodiment, each angled wall portion may transition into an adjacent angled wall portion at an angle less than about 30° or greater than about 150°. In a particular embodiment, angled wall portions 160 and end wall portions 162 are integrated to provide smooth transition points or lines. As such, each baffle element 154 has a smooth transition from one portion to another portion thereof.

Baffle elements 154 are positioned within body 152 such that at least one end wall portion 162 is substantially parallel to corresponding end portions of adjacent baffle elements 154, and adjacent baffle elements 154 define a tortuous path 168 therebetween. Referring to FIG. 4, a first baffle element 154 includes at least one angled area 170 defined at a transition line between adjacent angled wall portions 160 that extends toward a cooperating similar angled area 170 of a second adjacent baffle element 154 to define a portion of tortuous path 168. A width of the first baffle element 154 overlaps a width of the second baffle element 154 in a direction 172 substantially perpendicular to elongated baffle elements 154. As such, tortuous path 168 defined at least partially by cooperating angled areas 170 facilitates preventing or restricting ultraviolet light and/or visible light from passing through tortuous path 168. In one embodiment, as the ultraviolet light is deflected by angled wall portions 162, light absorbing material coated on baffle elements 154 absorbs at least a portion of the ultraviolet light. As such, light trap 130 substantially blocks ultraviolet light and/or other visible light from exiting chamber 106 while providing a sufficient flow path for air to channel through light tap 130. In a particular embodiment, light trap 130 and/or light trap 131 is larger than corresponding air inlet 108 and/or outlet 112, shown in FIGS. 1 and 2, to increase the desired light blocking effect.

It is apparent to those skilled in the art and guided by the teachings herein provided that light trap 130 and/or light trap 131 may have any suitable dimensions such that light traps 130, 131 facilitate preventing or limiting ultraviolet light from passing through light trap 130, 131. In one embodiment, light trap 130 includes about 23 baffle elements 154 spaced at about 0.413 inch with respect to each other. Each baffle element 154 has a height of about 2 inches and an overlapping area at cooperating angled areas 170 of about 0.1 inch, with adjacent angled wall portions 162 positioned at an angle of about 73.7 degrees. In an alternative embodiment, light trap 130 includes 43 baffle elements 154 spaced at about 0.206 inch with respect to each other. Each baffle element 154 has a height of about 2 inches and an overlapping area at cooperating angled areas 170 of about 0.1 inch, with adjacent angled wall portions positioned at an angle of about 102.7 degrees. In a further alternative embodiment, light trap 130 includes 23 baffle elements 154 spaced at about 0.406 inch with respect to each other. Each baffle element 154 has a height of about 3 inches and an overlapping area at cooperating angled areas 170 of about 0.1 inch, with adjacent angled wall portions positioned at an angle of about 102.7 degrees.

Figure 5:
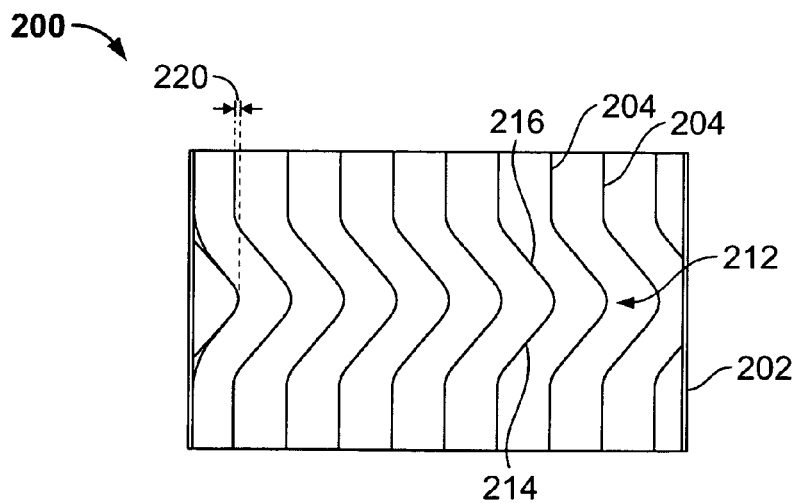
FIG. 5 is a sectional view of an alternative light trap suitable for use with the air treatment apparatus shown in FIG. 1.

FIG. 5 is a cross sectional view of an alternative light trap 200 suitable for use with air treatment apparatus 100 shown in FIG. 1. Light trap 200 is similar to light traps 130 shown in FIG. 3. Light trap 200 also includes a trap body 202 surrounding a plurality of integrated baffle elements 204. Each baffle element 204 includes an angled portion 212 having a first angled wall portion 214 transitioning into a second adjacent angled wall portion 216 at a suitable angle, such as an obtuse angle.

It is apparent to those skilled in the art and guided by the teachings herein provided that light trap 200 may have any suitable dimensions such that light trap 200 facilitate preventing or limiting ultraviolet light from passing through light trap 200. In one embodiment, light trap 200 includes 9 baffle elements 204 spaced at about 0.99 inch with respect to adjacent baffle elements 204. Each baffle element 204 has a height of about 6 inches and an overlapping area 220 of about 0.1 inch, with angled wall portion 214 positioned with respect to adjacent angled wall portion 216 at an angle of about 102 degrees. In an alternative embodiment, light trap 200 includes 18 baffle elements 204 spaced at about 0.5 inch with respect to adjacent baffle elements 204. Each baffle element 204 has a height of about 6 inches and an overlapping area 220 of about 0.1 inch, with angled wall portion 214 positioned with respect to adjacent angled wall portion 216 at an angle of about 133 degrees.

The above-described air treatment system allows the treatment and purification of air in an effective and reliable manner. More specifically, the air treatment system includes a helical ultraviolet lamp that provides a relatively higher ultraviolet dosage at a substantially uniform ultraviolet density within the system chamber. Further, the helical ultraviolet lamp can be used with light reflective material on the inner surface of at least a portion of the chamber to further improve performance. Additionally, in one embodiment the use of a single ultraviolet lamp according to the present invention reduces the number of the associated ballast, harness, and lamp holders required to operate the lamp, which simplifies the manufacture process. Further, the light traps of the present invention prevent or limit the escape of ultraviolet light from within the chamber, thus reducing undesirable duct material degradation and glowing within the duct.

Exemplary embodiments of an air treatment system are described above in detail. The apparatus is not limited to the specific embodiments described herein, but rather, components of the apparatus may be utilized independently and separately from other components described herein. Further, the described apparatus components can also be defined in, or used in combination with, other apparatus, and are not limited to practice with only the apparatus as described herein.

While the invention has been described in terms of various specific embodiments, those skilled in the art will recognize that the invention can be practiced with modification within the spirit and scope of the claims.

What is claimed is:

1. An air treatment system comprising:
    a housing defining a chamber, said housing further defining an air inlet at a first end portion of said housing and an air outlet at a second end portion of said housing opposing said first end portion, said chamber providing flow communication between said air inlet and said air outlet;
    at least one ultraviolet lamp positioned within said chamber, said at least one ultraviolet lamp positioned about a first axis and including a first end and a second end spaced with respect to said first end along the first axis, said at least one ultraviolet lamp configured for facilitating inactivating contaminants within air channeled through said chamber; and
    a light trap coupled to said housing with respect to at least one of said air inlet and said air outlet, said light trap comprising a plurality of adjacent baffle elements defining a tortuous path between adjacent baffle elements, each baffle element of said plurality of baffle elements positioned substantially parallel to the first axis, and a first baffle element of said plurality of adjacent baffle elements having a first width that overlaps a second width of an adjacent baffle element in a direction perpendicular to the first axis to prevent light generated by said at least one ultraviolet lamp from passing through the tortuous path.

2. An air treatment system in accordance with claim 1 wherein said at least one ultraviolet lamp further comprises a helical tube positioned about the first axis in a first translational direction.

3. An air treatment system in accordance with claim 1 wherein said at least one ultraviolet lamp defines an inner passage positioned about the first axis and configured to channel air through said chamber.

4. An air treatment system in accordance with claim 3 further comprising an outer passage defined between said at least one ultraviolet lamp and an interior surface of said housing.

5. An air treatment system in accordance with claim 1 wherein each baffle element of said plurality of baffle elements comprises an end wall portion substantially parallel to the first axis.

6. An air treatment system comprising:
    a housing defining a chamber, said housing further defining an air inlet at a first end portion of said housing and an air outlet at a second end portion of said housing opposing said first end portion, said chamber providing flow communication between said air inlet and said air outlet;
    at least one ultraviolet lamp positioned within said chamber, said at least one ultraviolet lamp configured for facilitating inactivating contaminants within air channeled through said chamber; and
    a light trap coupled to said housing with respect to at least one of said air inlet and said air outlet, said light trap configured to prevent light generated by said at least one ultraviolet lamp from exiting said housing, said light trap comprising a plurality of adjacent baffle elements defining a tortuous path between adjacent baffle elements, each baffle element of said plurality of baffle elements positioned substantially parallel to the first axis, and a first baffle element of said plurality of adjacent baffle elements having a first width that overlaps a second width of an adjacent baffle element in a direction perpendicular to the first axis to prevent light generated by said at least one ultraviolet lamp from passing through the tortuous path.

7. An air treatment system in accordance with claim 6 wherein said plurality of elongated baffle elements are positioned substantially parallel to each other.

8. An air treatment system in accordance with claim 7 wherein each said baffle element comprises at least two angled wall portions, each angled wall portion transitioning into an adjacent angled wall portion at an angle of about 30° to about 150°.

9. An air treatment system comprising:
    a housing defining a chamber along a first axis, said housing further defining an air inlet and an air outlet, said chamber providing flow communication between said air inlet and said air outlet;
    at least one ultraviolet lamp including a helical tube positioned within said chamber and extending about the first axis in a first translational direction, said at least one ultraviolet lamp configured for facilitating inactivating contaminants within air channeled through said chamber; and a light trap coupled to said housing with respect to at least one of said air inlet and said air outlet, said light trap comprising a plurality of adjacent baffle elements defining a tortuous path between adjacent baffle elements, each baffle element of said plurality of baffle elements positioned substantially parallel to the first axis, and a first baffle element of said plurality of adjacent baffle elements having a first width that overlaps a second width of an adjacent baffle element in a direction perpendicular to the first axis to prevent light generated by said at least one ultraviolet lamp from passing through the tortuous path.

10. An air treatment system in accordance with claim 9 wherein said at least one ultraviolet lamp defines an inner passage along the first axis, said inner passage facilitates channeling air between said air inlet and said air outlet.

11. An air treatment system in accordance with claim 9 wherein said light trap comprises a disc-shaped body surrounding said plurality of baffle elements.

12. An air treatment system in accordance with claim 9 wherein each said baffle element comprises a plurality of angled wall portions, and each said angled wall portion comprises a first part transitioning into a second part, said second part positioned at an obtuse angle with respect to said first part.

13. An air treatment system in accordance with claim 9 wherein at least one baffle element of said plurality of baffle elements is coated with a light absorbing material.

14. An air treatment system in accordance with claim 9 wherein at least one baffle element of said plurality of baffle elements comprises one of a light absorbing material and a light reflecting material.

15. An air treatment system in accordance with claim 9 wherein at least one baffle element of said plurality of baffle elements comprises an end wall portion substantially parallel to the first axis.

16. A method for assembling an air treatment system comprising:

providing a housing defining a chamber along a first axis, the housing further including an air inlet at a first end portion of the chamber and an air outlet at a second end portion of the chamber, the chamber defining an air passage providing flow communication between the air inlet and the air outlet;

positioning at least one ultraviolet lamp within the air passage, the at least one ultraviolet lamp positioned about the first axis and including a first end and a second end spaced with respect to the first end along the first axis, the at least one ultraviolet lamp configured for facilitating inactivating contaminants within air channeled through the air passage; and positioning at least one light trap with respect to at least one of the air inlet and the air outlet, the at least one light trap configured to contain ultraviolet light generated by the ultraviolet lamp within the housing, the at least one light trap comprising a plurality of adjacent baffle elements defining a tortuous path between adjacent baffle elements, each baffle element of the plurality of baffle elements positioned substantially parallel to the first axis, and a first baffle element of said plurality of adjacent baffle elements having a first width that overlaps a second width of an adjacent baffle element in a direction perpendicular to the first axis to prevent light generated by said at least one ultraviolet lamp from passing through the tortuous path.

17. A method in accordance with claim 16 wherein said positioning an ultraviolet lamp further comprises positioning a helical ultraviolet lamp within the air passage.

18. A method in accordance with claim 16 further comprising coating at least a portion of an inner surface of the chamber with a light reflective material.

19. A method in accordance with claim 16 wherein each baffle element of the plurality of baffle elements comprises an end wall portion substantially parallel to the first axis.

* * * * *